United States Patent [19]
Pagedas et al.

[11] Patent Number: 5,685,877
[45] Date of Patent: Nov. 11, 1997

[54] MUTIPLE TOOL LAPAROSCOPIC SURGICAL INSTRUMENT

[75] Inventors: Anthony Pagedas, 8401 W. Edgerton, Greendale, Wis. 53129; Fred L. Engle, Milwaukee, Wis.

[73] Assignee: Anthony Pagedas, Greendale, Wis.

[21] Appl. No.: 530,023

[22] Filed: Sep. 19, 1995

[51] Int. Cl.$^6$ ..................................... A61B 17/36
[52] U.S. Cl. ................. 606/46; 606/34; 606/41; 600/106; 600/108
[58] Field of Search ................. 606/34, 41–52; 600/104, 106, 153

[56] References Cited

U.S. PATENT DOCUMENTS

| 4,644,950 | 2/1987 | Valli ........................................ 606/46 |
| 5,186,714 | 2/1993 | Boudreault et al. . |
| 5,195,958 | 3/1993 | Phillips . |
| 5,449,356 | 9/1995 | Walbrink et al. ........................ 606/40 |

FOREIGN PATENT DOCUMENTS

| 2037139 | 10/1991 | Canada . |
| 2042456 | 11/1991 | Canada . |
| 9212680 | 8/1992 | WIPO ........................................ 606/39 |

*Primary Examiner*—David M. Shay
*Attorney, Agent, or Firm*—Ormiston Korfanta Dunbar & Holland

[57] ABSTRACT

A multiple tool laparoscopic surgical instrument that includes a hand piece, an outer conduit connected to the hand piece, four inner conduits within the outer conduit, an interior channel within the outer conduit, a hypodermic needle housed at least partially within a first one of the inner conduits, an electrocautery cutting tool housed at least partially within a second one of the inner conduit, and a needle electrode housed at least partially within a third one of the inner conduits. In operation, the interior channel of the outer conduit, which is connected to an external source of irrigating fluid and a suction device, is used to provide gentle irrigation as well as suction. A fourth one of the inner conduits, which preferably has a cross sectional area smaller than that of the interior channel of the outer conduit, is also connected to an external source of irrigating fluid to provide more vigorous irrigation. The hypodermic needle, electrocautery cutting tool and the needle electrode are individually and selectively extended and retracted to perform desired surgical tasks with each such tool.

11 Claims, 3 Drawing Sheets

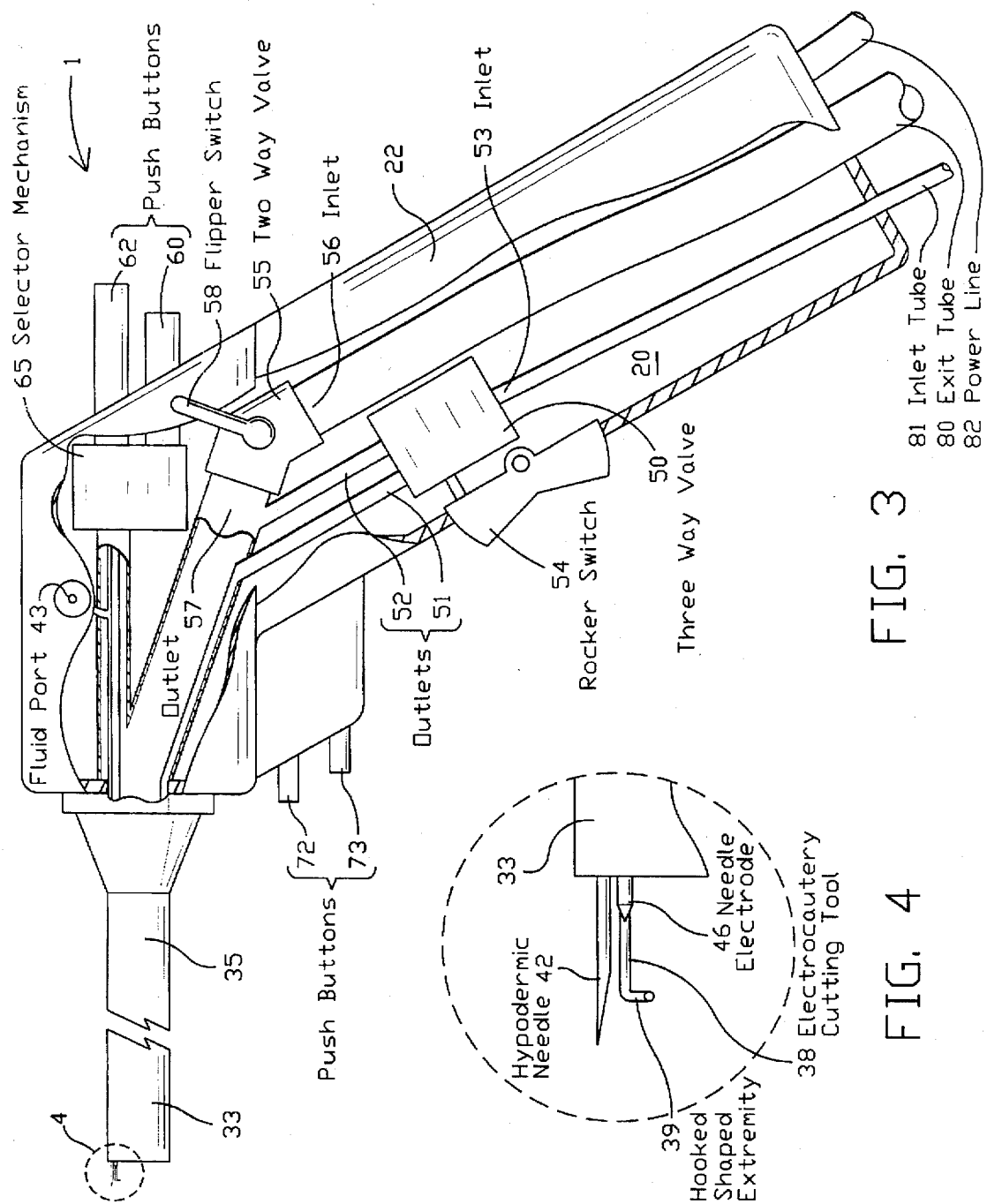

MUTIPLE TOOL LAPAROSCOPIC SURGICAL INSTRUMENT

DESCRIPTION

BACKGROUND OF THE INVENTION

1. Technical Field

The present invention relates to a multiple tool surgical instrument for use in laparoscopic surgeries.

2. Background

Laparoscopic surgery relates generally to a method of surgery that includes making only small incisions in the abdominal cavity and utilizing laparoscopic instruments to perform procedures in an essentially closed and intact abdominal cavity. The laparoscope, which includes a fiber optic light source and a video camera, allows the surgeon to view the internal organs and tissues, etc., within the abdominal cavity. In conjunction with the laparoscope, one or more surgical tools are used through additional small incisions. The tools are coordinated with the laparoscope to perform a variety of surgical procedures. One of the major advantages of laparoscopic surgery is that it allows surgery to be performed through much smaller incisions than are necessary in surgeries that require a surgeon to be able to fit their hands through the incision. The smaller incision of a laparoscopic surgery reduces the health risks attendant to the surgery, decreases the likelihood of surgery-related adhesions, hastens patient recovery from surgery and shortens, in most instances, the amount of time required to perform the surgical procedure.

The major disadvantage of laparoscopic surgery is the constraint of space and movement that is imposed by the small incisions. For many procedures a total of three incisions are made. In this style of surgery, the laparoscope is positioned through one incision and two separate surgical instruments are inserted through the other incisions. The surgeon must then either try to manipulate two instruments with one hand or engage an assistant to handle one of the three instruments. The disadvantage of the surgeon manipulating all three instruments is that the surgeon will have greatly reduced control and dexterity over the instruments. The disadvantage of engaging a surgical assistant to handle one or more of the instruments is that the surgeon loses the ability to naturally coordinate eye and hand movement in the procedure.

There have been a number of solutions proposed to alleviate these problems. U.S. Pat. No. 5,186,714 issued to Boudreault et al. employs a laparoscopic instrument that allows interchangeable cartridges which can include a cartridge for single direction fluid flow or a cartridge with electrodes or laser fibers. Interchanging cartridges during surgery can still require that the instrument must be moved and/or repositioned. U.S. Pat. No. 5,195,958 issued to Phillips also provides an instrument that permits laser or electrocautery in combination with a single direction fluid flow. These tools still have a limited number of functions. They do not allow for an area to be flushed or irrigated with fluid and the fluid to be simultaneously suctioned away during a procedure. These tools also do not provide a means for performing procedures other than single direction fluid flow and electrocautery.

SUMMARY OF THE INVENTION

It is one object of the present invention to provide a laparoscopic surgical instrument that includes multiple tools and functions in a configuration that is easy to manipulate and control.

Another object of the invention is to provide a laparoscopic surgical instrument that allows the contemporaneous washing of an area and removal of fluid, through a combination of fluid irrigation and suction.

A further object is to provide a laparoscopic surgical instrument that includes a means for both gentle and vigorous irrigation.

It is also an object of the invention to provide a laparoscopic instrument that allows selective extension and retraction of multiple tools housed within the instrument.

It is another object to provide a laparoscopic instrument that includes multiple surgical tools in one housing including an electrocautery cutting tool, a hypodermic needle, and a needle electrode.

These and other objects and advantages are achieved by a multiple tool laparoscopic surgical instrument that includes a hand piece, an outer conduit connected to the hand piece, four inner conduits within the outer conduit, an interior channel within the outer conduit, a hypodermic needle housed at least partially within a first one of the inner conduits, an electrocautery cutting tool housed at least partially within a second one of the inner conduits, and a needle electrode housed at least partially within a third one of the inner conduits. In operation, the interior channel of the outer conduit, which is connected to an external source of irrigating fluid and a suction device, is used to provide gentle irrigation as well as suction. A fourth one of the inner conduits, which preferably has a cross sectional area smaller than that of the interior channel of the outer conduit, is also connected to an external source of irrigating fluid to provide more vigorous irrigation and water dissection. The hypodermic needle, electrocautery cutting tool and the needle electrode are individually and selectively extended and retracted to perform desired surgical tasks.

In one aspect of the invention, the hand piece includes: a selector mechanism for extending a single selected tool from any of the inner conduits and simultaneously retracting the non-selected tools; an electrification mechanism for selectively electrifying the cutting rod and the needle electrode; a fluid port communicating with the hypodermic needle; a three way valve operatively coupled to the interior channel and to the fourth inner conduit, the three way valve being operative between two open positions for directing the flow of irrigation fluid selectively between the interior channel and the fourth inner conduit and a closed position wherein the irrigation fluid is prevented from flowing to either of the interior channel or the fourth inner conduit; and a two way valve operatively coupled to the interior channel, the two way valve being operative between an open position enabling suction removal of fluids through the interior channel and a closed position preventing suction removal of fluids.

Additional novel features and details of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

FIG. 3 is a cut away view of the hand piece illustrating the interior to the hand piece.

FIG. 4 is a side view detail of the distal end of the outer conduit illustrating the laparoscopic tools in the extended position.

DETAILED DESCRIPTION OF THE INVENTION

Figure 1:
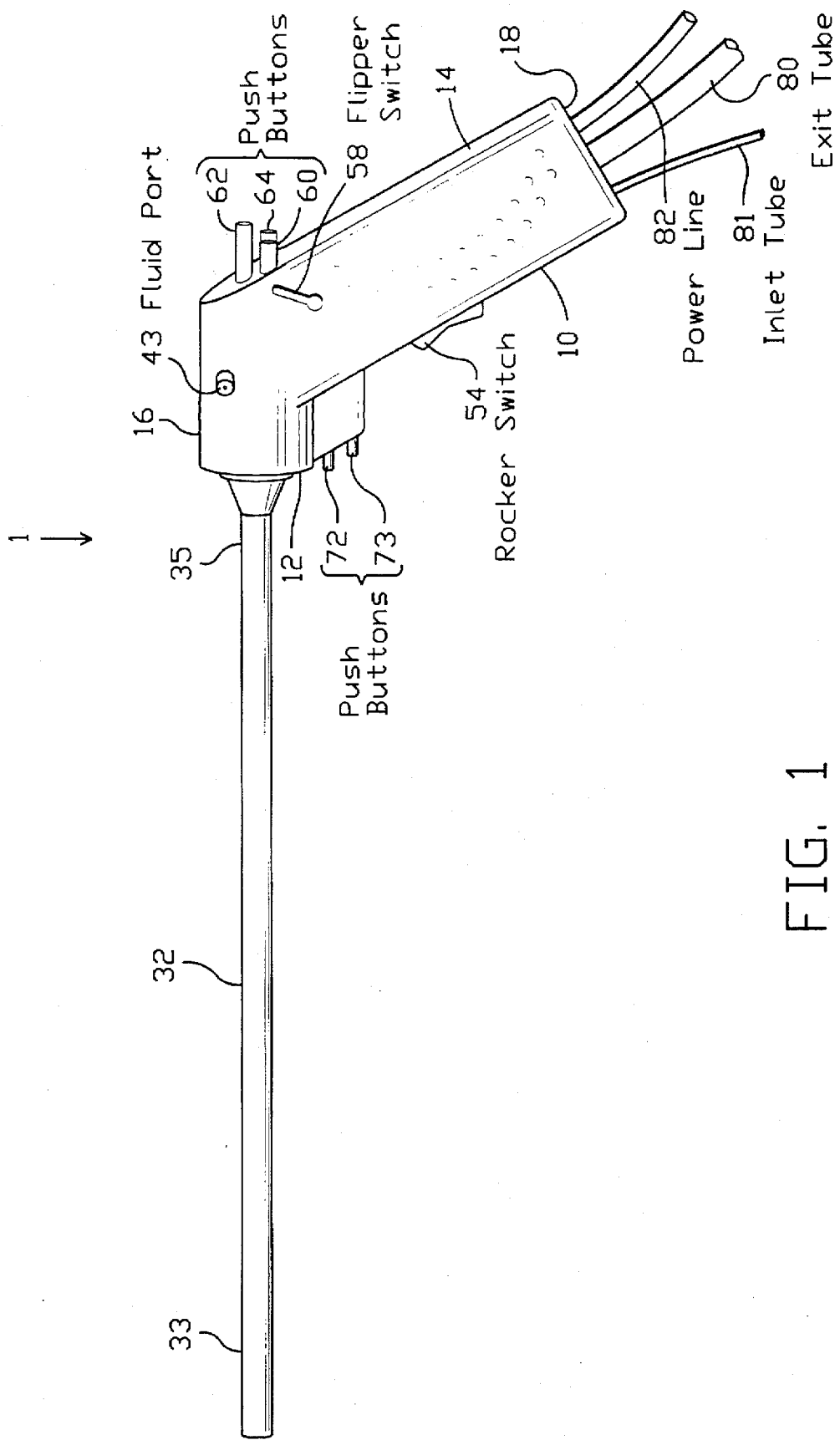
FIG. 1 is a perspective view of the preferred embodiment of the multiple tool laparoscopic surgical instrument illustrating the outer conduit and the hand piece.
Figure 2:
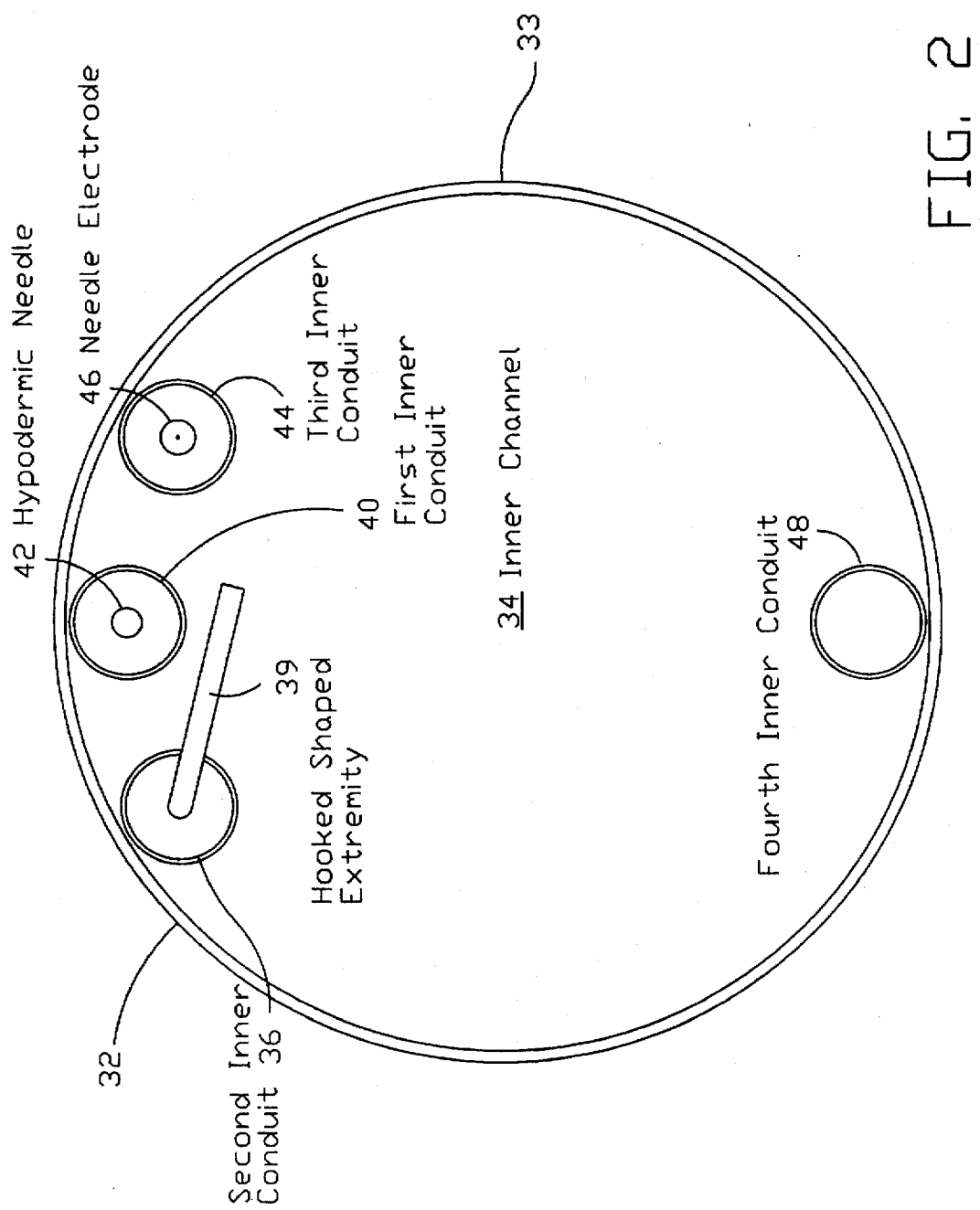
FIG. 2 is a distal end view of the outer conduit illustrating the interior channel, the plurality of inner conduits and the laparoscopic surgical tools.

Referring to FIGS. 1–3, the multiple tool laparoscopic instrument 1 according to the present invention is comprised generally of hand piece 10 and outer conduit 32. Hand piece 10 includes a front 12, a back 14, a top 16, a bottom 18, a first side 20 and a second side 22. Preferably, outer conduit 32 has an outer diameter of less than 9.8 mm to allow it to fit within a standard 10 mm laparoscopic trocar. The front 12 of hand piece 10 is attached to the proximal end 35 of outer conduit 32. Outer conduit 32 contains three, and preferably four smaller diameter inner conduits. Preferably, the inner conduits are sized and shaped so that the cross sectional area of interior channel 34 of outer conduit 32 is between one-half and two thirds of the cross sectional area of outer conduit 32. Interior channel 34 extends from distal end 33 of outer conduit 32 to proximal end 35 of outer conduit 32.

Referring now specifically to FIGS. 2 and 3, first inner conduit 40, which houses hypodermic needle 42, is located in the interior of outer conduit 32, preferably at the 12 o'clock position when viewed from distal end 33 of outer conduit 32. First inner conduit 40 extends from distal end 33 to proximal end 35 and into hand piece 10. A second inner conduit 36, which houses electrocautery cutting tool 38, is located in the interior of outer conduit 32, preferably adjacent to first inner conduit 40 in the 11 o'clock position when viewed from distal end 33 of outer conduit 32. Second inner conduit 36 extends from distal end 33 to proximal end 35 and into handpiece 10. A third inner conduit 44, which houses needle electrode 46, is located in the interior of outer conduit 32, preferably adjacent to first inner conduit 40 in the 1 o'clock position as viewed from distal end 33 of outer conduit 32. Third inner conduit 44 extends from distal end 33 to proximal end 35 and into handpiece 10. A fourth inner conduit 48, which serves as a channel for the conveyance of fluid for vigorous irrigation, is located in the interior of outer conduit 32, preferably opposite first inner conduit 40 in the 6 o'clock position when viewed from distal end 33 of outer conduit 32. Fourth inner conduit 48 extends from distal end 33 to proximal end 35 and into handpiece 10.

Referring now to FIGS. 1–4, electrocautery cutting tool 38 preferably includes a hooked shaped extremity 39. Hypodermic needle 42, cutting tool 38 and electrode 46 are each individually extendible and retractable out of and into first inner conduit 40, second inner conduit 36 and third inner conduit 44, respectively, through the operation of selector mechanism 65 and push buttons 62, 60 and 64. For convenience of operation, push buttons 62, 60 and 64 are located near the top 16 of the back 14 of hand piece 10 in the 12 o'clock, 1 o'clock and 11 o'clock positions, respectively, when viewed from the back of the hand piece. Push buttons 62, 60 and 64 operate in cooperation with selector mechanism 65 so that depression of any one of the push buttons results in a latching of the push button in the depressed position and extension of the corresponding tool, and the simultaneous retraction of any previously extended tools and the corresponding return of any previously depressed buttons to the extended position. Any suitable extension/retraction mechanism may be used, such as that used in a conventional three-way ball point pen.

In the preferred embodiment of the invention, selective application of electrical power to the electrocautery cutting tool 38 and the needle electrode 46 is controlled by first power control push button 72 and second power control push button 73, respectively. First and second power control push buttons 72 and 73 are located on the front 12 of hand piece 10 and move between a depressed position and an extended position. Using a conventional extension/retraction mechanism such as that used in a ball point pen, each power control push button locks into the depressed position when it is pushed in and automatically releases to the extended position from the depressed position when it is pushed in again. Preferably, first and second power control push buttons 72 and 73 are configured so that, in the event both buttons are depressed, no electrical power is delivered to either electrocautery tool. Alternatively, and again using a conventional mechanism such as that used in a three way ball point pen, power control push buttons 72 and 73 are configured so that only one button may be depressed at any given time and correspondingly, electrical current will flow to only one electrocautery tool at a time. Electrical power is delivered to hand piece 10 through power line 82 using a conventional power source (not shown). Alternatively, power control for electrocautery tools 38 and 46 may be provided by a foot pedal control, as found in conventional surgical electrocautery instruments.

The selective electrification of electrocautery cutting tool 38 allows for the electrocautery angled cutting tool to be optionally used for simultaneous cutting of tissue and cautery, primarily to seal small vessels that leak blood during tissue cutting. The selective electrification of electrocautery cutting tool 38 also provides other advantages. For example, it allows for isolating selected tissue on the electrocautery cutting tool 38 and performing the cutting or severing of the tissue by applying electrical power to electrocautery cutting tool 38. Different surgeries, for example gall bladder surgery versus reproductive organ surgery, will dictate what combination of cutting and optional cauterization is appropriate when using electrocautery cutting tool 38.

Hypodermic needle 42 preferably extends the length of inner conduit 40. Needle 42 may be characterized as a small gage/bore cannula and can have either a blunt or beveled tip. The proximal end of hypodermic needle 42 communicates with fluid port 43. The connection of a syringe (not shown) to fluid port 43 allows the hypodermic needle 42 to be used for both injection and aspiration. Hypodermic needle 42 is connected in such a manner that different hypodermic needles can be selected and installed prior to or between surgical applications. For example, a blunt tip or atraumatic needle would often be selected for puncturing the wall of a uterus to introduce fluid, while a beveled tip needle might be a more desirable choice for aspiration of ovarian follicles or cysts. Conventional means by which hypodermic needle 42 may be installed include a threaded connection, bayonet-style mounting, Luer-lock mounting and the like.

Needle electrode 46 can have a blunt atraumatic distal tip or a sharpened cutting distal tip depending in the predetermined selected use in a procedure. As with hypodermic needle 42, electrocautery rod 46 is installed by any of the above described conventional means, or other suitable means, to permit its replacement or substitution between uses of instrument 1. Fourth inner conduit 48 provides for vigorous irrigation. Fourth inner conduit 48 has a cross sectional area less than one half, and preferably less than one third, that of outer conduit 32. In the preferred embodiment, fourth inner conduit 48 is less than one third the diameter of outer conduit 32.

Referring now specifically to FIG. 3, a three way valve 50, which has first and second outlets 51 and 52 and a first inlet 53, selectively directs the flow or irrigation fluid between fourth inner conduit 48 and interior channel 34. The proximal end of fourth inner conduit 48 is operatively coupled to first outlet 51. The proximal end of interior channel 34 is operatively coupled to second outlet 52. Three way valve 50 may be operated in any conventional manner such as through rocker switch 54, which selectively opens and closes first and second outlets 51 and 52, to direct irrigation fluid to fourth inner conduit 48 for vigorous irrigation through first outlet 51 or to interior channel 34 for gentle irrigation through second outlet 52. For convenient operation, rocker switch 54 is preferably positioned on front 12 of hand piece 10. Irrigation fluid is supplied to hand piece 10 through inlet tube 81. Any appropriate pumping mechanism can be used, such as a piston-driven pump, a peristaltic pump, and the like.

Alternatively, fourth inner conduit 48 may be located outside of outer conduit 32. The distal end of fourth inner conduit 48 may, in addition, be recessed from distal end 33 of outer conduit 32. This configuration allows irrigation fluid discharged from fourth inner conduit 48 additional contact time with tissue surfaces before optional removal through interior channel 34.

Interior channel 34 is optionally useable for removal of fluids or conveyance or irrigation fluid therethrough. A two way valve 55, which includes second inlet 56 and third outlet 57, enables the use of interior channel 34 for the removal of fluids. The proximal end of interior channel 34 is operatively coupled to third outlet 57. Fluid is removed by any suitable suction device connected to exit tube 80. Two way valve 55 is preferably operated by means of flipper switch 58 which selectively opens and closes third outlet 57. For convenient operation, flipper switch 58 is preferably positioned on second side 22 of hand piece 10.

The connections from the electrical power source to electrocautery cutting tool 38 and needle electrode rod 46 are configured so that the opening of first, second or third outlets 51, 52 or 57 interrupts the flow of electrical power to these electrocautery tools.

The multiple tool laparoscopic instrument of the present invention allows the simultaneous irrigation and suction of fluid which provides new options with a single instrument. For example, an area can be washed and suctioned for improved visualization or an area can be flushed and suctioned to collect objects such as small gall stones, embryos and the like. In addition, the invented instrument provides numerous tools in one housing that are often used in laparoscopic surgeries, thus allowing the surgeon to alternate tools without having to remove one instrument and re-insert and re-orient another. With the improved features of the present invention surgeries can be performed more efficiently and more effectively,

What is claimed is:

1. A multiple tool laparoscopic surgical instrument, comprising:

a hand piece;

b. an outer conduit attached to the hand piece, the outer conduit defining an interior region having disposed therein an interior channel for fluid suction or irrigation, a first inner conduit housing an extendible and retractable hypodermic needle tool, a second inner conduit housing an extendible and retractable electrocautery cutting tool, and a third inner conduit housing an extendible and retractable needle electrode tool;

c. a fourth conduit attached to the hand piece and positioned adjacent and parallel to the outer conduit; and d. the hand piece further including: an attached selector means for extending a single selected tool from any of the inner conduits and simultaneously retracting any extended non-selected tools; and an electrification means electrically connected to the electrocautery tool and the needle electrode, for selectively electrifying the electrocautery cutting tool and the needle electrode.

2. The instrument of claim 1, wherein the fourth conduit is an inner conduit disposed within the interior region of the outer conduit.

3. The instrument of claim 1, wherein the selector means comprises first, second, and third push buttons operatively coupled to the electrocautery cutting tool, the hypodermic needle tool, and the needle electrode tool, respectively, each of the push buttons being operative between a depressed position wherein the tool coupled thereto is extended and any previously extended tools are simultaneously retracted and a non-depressed position wherein the tool coupled thereto is retracted.

4. The instrument of claim 1, wherein the electrification means electrifies the electrocautery cutting tool and the needle electrode tool only when the tools are extended.

5. The instrument of claim 1, further comprising:

a. a three way valve operatively coupled to the interior channel and to the fourth conduit, the three way valve being operative between two open positions for directing the flow of irrigation fluid selectively between the interior channel and the fourth conduit and a closed position wherein the irrigation fluid is prevented from flowing to either the interior channel or the fourth conduit; and b. a two way valve operatively coupled to the interior channel, the two way valve being operative between an open position enabling suction removal of fluids through the interior channel and a closed position preventing suction removal of fluids.

6. The instrument of claim 5, wherein the hand piece further includes an inlet tube connected to the three easy valve for supplying irrigation fluid to the interior channel and the fourth inner conduit.

7. The instrument of claim 5, wherein the hand piece further includes an exit tube connected to the two way valve for removing suction fluid through the interior channel.

8. The instrument of claim 1, wherein the hand piece further includes a fluid port communicating with the hypodermic needle.

9. The instrument of claim 8, wherein the fluid port further includes an attached adapter to receive a hypodermic syringe.

10. A multiple tool laparoscopic surgical instrument, comprising:

a. a hand piece having a top, a bottom, at least one sidewall extending between the top and bottom, an interior chamber bounded by the top, bottom and sidewall, and a longitudinal axis oriented substantially parallel to a plane defined by the sidewall;

b. an outer conduit having a cross sectional area, the outer conduit defining an interior region therein, the outer conduit having a distal end, a proximal end and a longitudinal axis, the proximal end of the outer conduit being connected to the hand piece so that the longitudinal axis of the outer conduit intersects the longitudinal axis of the hand piece and the interior region communicates with the interior chamber;

c. a first inner conduit disposed within the interior region and extending from the distal end of the outer conduit to the proximal end of the outer conduit;

d. a second inner conduit disposed within the interior region and extending from the distal end of the outer conduit to the proximal end of the outer conduit;

e. a third inner conduit disposed within the interior region and extending from the distal end of the outer conduit to the proximal end of the outer conduit;

f. a fourth inner conduit having a cross sectional area, the inner conduit disposed within the interior region and extending from the distal end of the outer conduit to the proximal end of the outer conduit;

g. an interior channel within the outer conduit, the interior channel being nominally defined by a volume interior to the outer conduit and exterior to the first, second, third and fourth inner conduits;

h. a hypodermic needle tool housed at least partially within the first inner conduit;

i. an electrocautery cutting tool housed at least partially within the second inner conduit: and j. a needle electrode tool housed at least partially within the third inner conduit:

k. each of the hypodermic needle, electrocautery cutting and needle electrode tools selectively moveable between an extended position wherein the tool is available for use and a retracted position wherein the tool is not available for use: and l. a selector means operatively coupled to the tools for extending a single selected tool from any of the inner conduits and simultaneously retracting the non-selected tools.

11. The instrument of claim 10, wherein the selector means comprises first, second, and third push buttons operatively coupled to the electrocautery cutting tool, the hypodermic needle tool, and the needle electrode tool, respectively, each of the push buttons being operative between a depressed position wherein the tool coupled thereto is extended and any previously extended tools are simultaneously retracted and a non-depressed position wherein the tool coupled thereto is retracted.

* * * * *